(12) United States Patent
Haas

(10) Patent No.: US 10,030,254 B2
(45) Date of Patent: Jul. 24, 2018

(54) MAXIMIZING PRODUCTION OF HYDROGEN FROM WASTE MATERIALS BY ACTIVE REMOVAL OF HYDROGEN

(71) Applicant: Charles Nathan Haas, Philadelphia, PA (US)

(72) Inventor: Charles Nathan Haas, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/324,605

(22) PCT Filed: Sep. 2, 2015

(86) PCT No.: PCT/US2015/048180
§ 371 (c)(1),
(2) Date: Jan. 6, 2017

(87) PCT Pub. No.: WO2016/040074
PCT Pub. Date: Mar. 17, 2016

(65) Prior Publication Data
US 2017/0204434 A1  Jul. 20, 2017

Related U.S. Application Data

(60) Provisional application No. 62/049,163, filed on Sep. 11, 2014.

(51) Int. Cl.
C12P 3/00 (2006.01)
C01B 3/50 (2006.01)
(Continued)

(52) U.S. Cl.
CPC .............. *C12P 3/00* (2013.01); *C01B 3/501* (2013.01); *C01B 3/56* (2013.01); *C12M 21/04* (2013.01);
(Continued)

(58) Field of Classification Search
CPC ........................................................ C12P 3/00
See application file for complete search history.

(56) References Cited

U.S. PATENT DOCUMENTS 4,696,746 A    9/1987   Ghosh et al.
4,920,055 A    4/1990   Hoiberg et al.
(Continued)

FOREIGN PATENT DOCUMENTS

WO    WO2009070273 A1    6/2009
WO    WO2011084994 A1    7/2011

OTHER PUBLICATIONS

Parkin, Gene F., and William F. Owen. "Fundamentals of anaerobic digestion of wastewater sludges." Journal of Environmental Engineering 112.5 (1986): 867-920.
(Continued)

*Primary Examiner* — Rosanne Kosson
(74) *Attorney, Agent, or Firm* — Mendelsohn Dunleavy, P.C.

(57) ABSTRACT

The present invention provides a method of producing hydrogen from a waste material, comprising steps of fermenting 100 a fermentation mixture comprising the waste material in a reactor 1 with a headspace 1a under anaerobic conditions, removing 200 hydrogen from a gas from the headspace 1a during fermentation to produce a hydrogen gas and a remainder gas and recirculating 300 at least a portion of the remainder gas back to the headspace 1a. An apparatus for producing hydrogen and recirculating at least a portion of the remainder gas to the headspace 1a is also provided.

20 Claims, 2 Drawing Sheets

(51) Int. Cl.
  *C01B 3/56* (2006.01)
  *C12M 1/107* (2006.01)
  *C12M 1/00* (2006.01)
  *C12M 1/34* (2006.01)

(52) U.S. Cl.
  CPC ............ *C12M 29/04* (2013.01); *C12M 29/24* (2013.01); *C12M 41/12* (2013.01); *C12M 41/26* (2013.01); *C12M 41/34* (2013.01); *C12M 47/18* (2013.01); *C01B 2203/041* (2013.01); *C01B 2203/0425* (2013.01)

(56) References Cited

U.S. PATENT DOCUMENTS

| | | | |
|---|---|---|---|
| 5,611,931 | A | 3/1997 | Liu et al. |
| 5,705,374 | A | 1/1998 | Sanford et al. |
| 5,834,264 | A | 11/1998 | Sanford et al. |
| 6,159,272 | A | 12/2000 | Baker et al. |
| 6,649,559 | B2 | 11/2003 | Drost et al. |
| 7,033,822 | B2 | 4/2006 | Maston |
| 7,575,624 | B2 | 8/2009 | Cartwright et al. |
| 7,897,207 | B2 | 3/2011 | Liu et al. |
| 7,901,916 | B2 | 3/2011 | Shin et al. |
| 8,093,041 | B1 * | 1/2012 | Nirmalakhandan ... C12M 21/04 435/289.1 |
| 8,282,707 | B2 | 10/2012 | Bresier et al. |
| 8,501,463 | B2 | 8/2013 | Cox et al. |
| 2007/0207531 | A1 | 9/2007 | Ferchichi et al. |
| 2011/0171117 | A1 | 7/2011 | Gorski et al. |
| 2013/0137153 | A1 * | 5/2013 | Elbeshbishy ............. C12P 3/00 435/168 |
| 2014/0157777 | A1 | 6/2014 | Kramer et al. |

OTHER PUBLICATIONS

Oh, Sang-Eun, Steven Van Ginkel, and Bruce E. Logan. "The relative effectiveness of pH control and heat treatment for enhancing biohydrogen gas production." Environmental science & technology 37.22 (2003): 5186-5190.
Chong, Mei-Ling, et al. "Biohydrogen production from biomass and industrial wastes by dark fermentation." International Journal of Hydrogen Energy 34.8 (2009): 3277-3287.
Huang, Chen-Chia, Hsiu-Mei Chen, and Chien-Hung Chen. "Hydrogen adsorption on modified activated carbon." International journal of hydrogen energy 35.7 (2010): 2777-2780.
Nugent, Patrick, et al. "Porous materials with optimal adsorption thermodynamics and kinetics for CO2 separation." Nature 495.7439 (2013): 80-84.
Suh, Myunghyun Paik, et al. "Hydrogen storage in metal-organic frameworks." Chemical reviews 112.2 (2011): 782-835.
Carta, Mariolino, et al. "An efficient polymer molecular sieve for membrane gas separations." Science 339.6117 (2013): 303-307.
Du, Huailiang, et al. "Separation of hydrogen and nitrogen gases with porous graphene membrane." The Journal of Physical Chemistry C 115.47 (2011): 23261-23266.
Li, Yan-Shuo, et al. "Molecular sieve membrane: supported metal-organic framework with high hydrogen selectivity." Angewandte Chemie 122.3 (2010): 558-561.
Grainger, David, and May-Britt Hägg. "The recovery by carbon molecular sieve membranes of hydrogen transmitted in natural gas networks." International Journal of Hydrogen Energy 33.9 (2008): 2379-2388.
Park, Wooshin, et al. "Removal of headspace CO2 increases biological hydrogen production." Environmental science & technology 39.12 (2005): 4416-4420.
International Search Report and Written Opinion; dated Nov. 30, 2015 for PCT Application No. PCT/US2015/048180.

* cited by examiner

US 10,030,254 B2

MAXIMIZING PRODUCTION OF HYDROGEN FROM WASTE MATERIALS BY ACTIVE REMOVAL OF HYDROGEN

BACKGROUND OF THE INVENTION

1. Field of the Invention

The present invention relates to the production of hydrogen from waste materials. In particular, the present invention is directed to a process of using anaerobic fermentation to maximize the production of hydrogen from waste materials.

2. Description of the Related Technology

Hydrogen is an important feedstock in industrial processes as well as a potential source of clean energy either by combustion or use in fuel cells. Hydrogen has the highest energy content per unit weight of any known fuel and can easily be converted to electric energy via fuel cell technology. In addition, hydrogen generates only water when combusted and therefore provides an environmentally-friendly option for energy generation. Therefore, hydrogen has been described as the fuel of the future (Serfass et al., "Practical hydrogen development strategy," *International Journal of Hydrogen Energy*, vol. 16, pages 551-556, 1991). Currently, more than 90% of commercial hydrogen is produced by steam reforming. In steam reforming, high temperature water/steam is reacted with hydrocarbons such as natural gas, thereby producing hydrogen and carbon dioxide. However this process uses fossil fuels as starting materials and thus is an energy intensive process.

Fermentation processes using microorganisms provide an environmentally friendly alternative means for hydrogen production. One drawback of this alternative is the low yield and its susceptibility to end-product inhibition of hydrogen production (Taguchi et al., "Hydrogen production from continuous fermentation of xylose during growth of *Clostridium* sp. strain No. 2," *Can. J. Microbiol.*, vol. 41, pages 536-540, 1995). This drawback makes this alternative uneconomical for commercial production of hydrogen. In addition, light is required in many of these fermentation processes, which makes large scale fermentation impractical in some circumstances.

It has also been proposed that anaerobic fermentation may be a practical alternative for hydrogen production because of its advantages such as its high yield of hydrogen, no requirement for light energy, and because this process is capable of using organic waste materials to provide nutrients for the microorganisms (Hawkes et al., "Sustainable fermentative hydrogen production: challenges for process optimization," *Int. J. Hydrogen Energ.*, vol. 27, pages 1339-1347, 2002).

U.S. Pat. No. 7,901,916 teaches a method for producing hydrogen by a batch fermentation process from pretreated organic waste as a substrate for microorganisms. The process comprises pretreating an organic waste and fermenting the pretreated organic waste under anaerobic conditions and with an initial pH of 7 to 9. This anaerobic fermentation process is operated in batch mode. The organic waste may be food waste, sewage sludge or livestock waste water. Pretreatment of the organic waste may be by heat treatment, an acid treatment, an alkali treatment or any combination thereof.

U.S. Pat. No. 8,501,463 discloses a method for producing chemicals by anaerobically fermenting biomass using anaerobic bacteria. The chemicals that may be produced include hydrogen gas, volatile organic acids, solvents, solids, and salts of volatile organic acids. The biomass may be pretreated before the anaerobic fermentation step by one or more pretreatment techniques that include sterilization, deoxygenation, concentration, detoxificatipn, and/or predigestion. The biomass may be energy crops, surplus agricultural products, waste from sugar production and processing facilities, waste from fruit processing industries, waste from pulp and paper mills, silvaculture residues, waste from wood processing, waste from agricultural product processing, food waste, solids isolated from fermentation cultures, municipal sewage waste, animal manure, animal urine, and animal parts.

Parkin et al. ("Fundamentals of anaerobic digestion of wastewater sludges," *Journal of Environmental Engineering*, vol. 112, pages 867-920, 1986) provides a comprehensive discussion of anaerobic fermentation of municipal wastewater sludges to produce methane and hydrogen. The anaerobic fermentation process may be optimized by adjusting retention time, mixing conditions to maximize bacteria-substrate contact, pH and temperature, the type and amount of nutrients, removal of toxic materials, and feed ratios.

Oh et al. ("The Relative Effectiveness of pH Control and Heat Treatment for Enhancing Biohydrogen Gas Production," *Environ. Sci. Technol.*, vol. 37, pages 5186-5190, 2003) discloses a method for hydrogen production by fermentation of organic substrates at high concentrations while suppressing hydrogen transfer to methanogens by heat treatment, removing non-sporeforming methanogens from the inoculum, and lowering the pH of the fermentation process. It was found that low pH was, without the heat treatment, sufficient to prevent hydrogen losses to methanogens in a mixed batch fermentation.

Chong et al. ("Biohydrogen production from biomass and industrial wastes by dark fermentation," *International Journal of Hydrogen Energy*, vol. 34, pages 3277-3287, 2009) discloses a method for hydrogen production by dark fermentation of biomass. Suitable biomass for hydrogen production includes food and starch-based wastes, cellulosic materials, dairy wastes, palm oil mill effluent and glycerol. Hydrogen production is said to be enhanced by lowering hydrogen partial pressure during anaerobic biodegradation, possibly accompanied by pH control, $CO_2$ removal and pretreatment of the biomass. The hydrogen partial pressure may be lowered by either stripping with an inert gas or vigorous agitation of the fermentation medium.

U.S. Pat. No. 5,705,374 teaches a process for producing hydrogen and carbon dioxide from an anaerobic culture medium using a proteobacteria. The preferred proteobacteria is *Desulfovibrio* sp. ATCC 55738 (FOX1). The culture medium includes a carbon source selected from formic acid, a formate and mixtures thereof, a nitrogen source and vitamins.

US 2007/0207531 discloses a method for producing hydrogen by fermenting a culture medium containing sugar. The fermentation is maintained under substantially anaerobic conditions and employs a bacterium of the genus *Clostridium*, preferably *Clostridium bifermentans*. The disclosed method can produce hydrogen with an efficiency of at least about 34% relative to the maximum theoretical yield.

The present invention provides a method of hydrogen production through anaerobic fermentation of waste materials. The method removes hydrogen during the anaerobic fermentation, thereby reducing suppression of hydrogen production by the produced hydrogen. The method is capable of enhancing the yield and/or selectivity of hydrogen production.

SUMMARY OF THE INVENTION

In one aspect, the present invention provides a method of producing hydrogen from a waste material, comprising steps of fermenting 100 a fermentation mixture comprising the waste material in a reactor 1 with a headspace 1a under anaerobic conditions, separating 200 hydrogen from non-hydrogen components of the headspace gas during the fermentation step to produce a remainder gas, and continuing 300 the fermentation step with at least a portion of the non-hydrogen components of the remainder gas from which the hydrogen was separated, located in the reactor.

In another aspect, the method of the present invention also comprises a step of introducing at least one microorganism into the fermentation mixture.

In yet another aspect, the method of the present invention also comprises a step of maintaining the pH in the fermentation mixture to be substantially stable during the fermenting step 100.

In yet another aspect, the method of the present invention also comprises a step of monitoring the pH in the fermentation mixture continuously or periodically during the fermenting step 100.

In yet another aspect, the method of the present invention also comprises a step of adding a nitrogen source to the fermentation mixture.

In yet another aspect, the method of the present invention also comprises a pretreatment step before the fermenting step 100, wherein the pretreatment step is selected from a heat treatment, an acid treatment, an alkali treatment and combinations thereof.

In yet another aspect, the method of the present invention also comprises a step of removing carbon dioxide from the headspace gas.

In yet another aspect, the method of the present invention comprises removing headspace gas from the reactor headspace, separating hydrogen, and optionally, carbon dioxide, from the removed headspace gas and recirculating the remainder of the removed headspace gas to the reactor.

In yet another aspect, the present invention provides an apparatus for hydrogen production, comprising a reactor 1 suitable for anaerobic fermentation and having a headspace 1a, a hydrogen removal device 3 for selectively removing hydrogen from a headspace gas to produce hydrogen gas and a remainder gas, and, optionally, a fluid communication system 2 in fluid communication with the headspace 1a and the hydrogen removal device 3 for returning at least a portion of the remainder gas to the headspace 1a, if the hydrogen is removed from the remainder gas outside of the headspace 1a.

In yet another aspect, the apparatus of the present invention also comprises a pump for generating a gas flow in the fluid communication system 2.

In yet another aspect, the apparatus of the present invention also comprises at least one sensor selected from a temperature sensor in the reactor 1, a pH sensor for measuring pH of a fermentation mixture in the reactor, a sensor of measuring hydrogen partial pressure in a headspace 1a of the reactor 1, a sensor for measuring a velocity of a gas stream in the fluid communication system 2 and any combination thereof.

DEFINITIONS

Figure 1A:
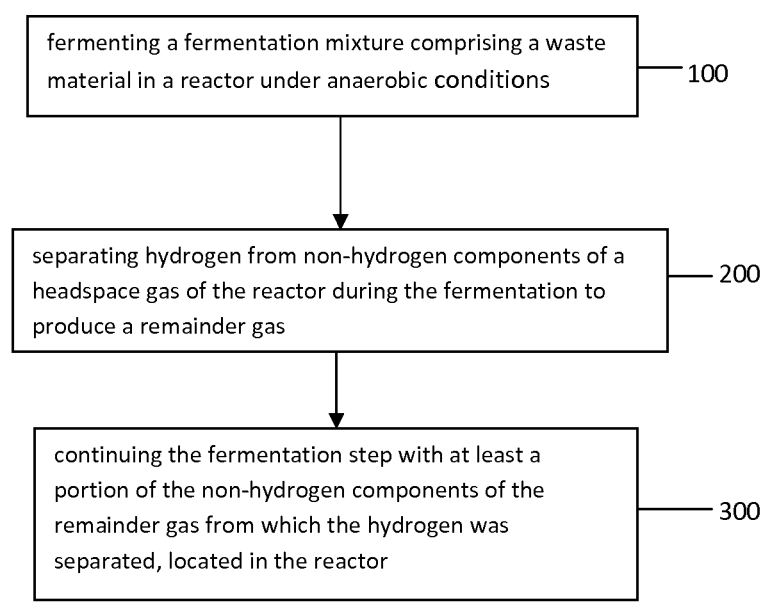
FIG. 1A is a flow chart that shows a method for generating hydrogen from a fermentation mixture comprising a waste material, according to one embodiment of the present invention.

The term "anaerobic" or "anoxic" as used herein refers to an environment in which there is little or no free oxygen available. By way of example only, the oxygen concentration in the environment may be less than 10,000 ppm, or less than 1,000 ppm, or less than 100 ppm, or less than 50 ppm, or less than 20 ppm.

The term "anaerobic fermentation" as used herein refers to an anaerobic process in which a waste material is degraded by microorganisms to chemical products such as hydrogen, carbon dioxide, volatile organic acids, hydrogen sulfide, methane, and carbon monoxide.

The term "nitrogen source" as used herein means any source of nitrogen that can be utilized by microorganisms, which includes organic and inorganic nitrogen compounds. Examples include nitrates, nitrites, ammonium salts, amino compounds, proteins and amino acids and derivatives, compounds and complexes thereof. Such nitrogen sources may be supplied in pure, semi-pure, or mixed form and may be included as components of hydrolyzed or unhydrolyzed extracts of plants, animals, yeasts or other organisms.

The terms "waste" and "waste material," used herein interchangeably, mean any source of carbon or sugars which may be generally unwanted, unusable or undesirable. They include materials which are not a primary desired product of an activity and are not produced primarily for sale or use. Examples include, but not limited to, municipal waste, industrial waste, domestic waste, agro-industrial waste, agricultural waste, farm waste, food processing waste, meat waste, paper waste, brewing waste, dairy waste, all types of plant material waste including products such as corn cobs, nut shells, husks, vegetable waste, fruit peels and seeds, plant waste, berry processing fiber, apple processing waste, and raspberry processing waste, all types of dairy waste including products such as spoilt milk, cheese and whey, brewing waste such as yeast residue, pulp and paper mill waste, sugar cane bagasse, newspaper print fiber, cellulose, hemi-cellulose, and fibrous waste. The waste may be hydrolyzed or unhydrolyzed, treated or untreated. The waste may include mixtures containing one or more of the foregoing.

The term "yield" as used herein means, with respect to hydrogen production, the number of moles of hydrogen produced per unit of the waste material.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

In one aspect, the present invention provides a method of producing hydrogen from a waste material, comprising steps of fermenting 100 a fermentation mixture comprising the waste material in a reactor 1 with a headspace 1a under anaerobic conditions, separating 200 hydrogen from non-hydrogen components of the headspace gas during the fermentation step to produce a remainder gas, and continuing 300 the fermentation step with at least a portion of the non-hydrogen components of the headspace gas from which the hydrogen was separated, located in the reactor (FIG. 1A).

Figure 1B:
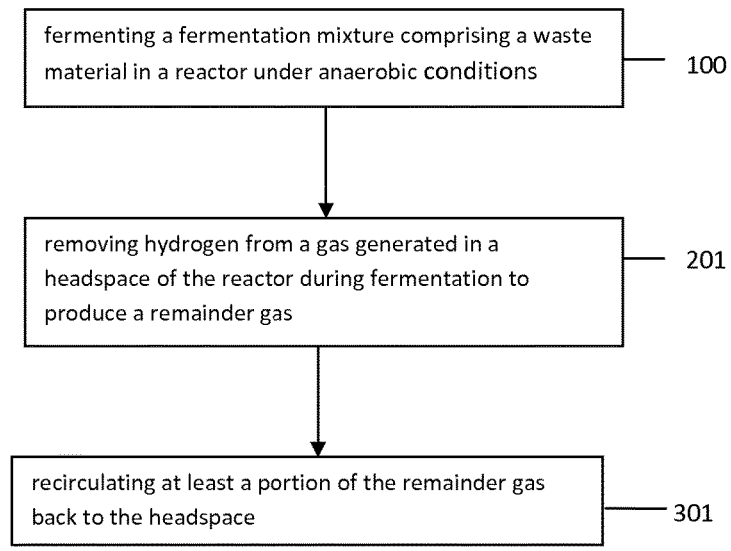
FIG. 1B is a flow chart that shows another method for generating hydrogen from a fermentation mixture comprising a waste material, according to a different embodiment of the present invention where hydrogen is separated from the headspace gas to provide a remainder gas at a location outside the headspace of the reactor and the remainder gas is recirculated to the reactor.

In another aspect, the method of producing hydrogen from a waste material comprises fermenting 100 a fermentation mixture comprising the waste material in a reactor 1 with a headspace 1a under anaerobic conditions, removing 201 hydrogen from a gas in the headspace 1a during the fermentation to produce hydrogen and a remainder gas, and recirculating 301 at least a portion of the remainder gas back to the headspace 1a of the reactor 1 (FIG. 1B).

The waste material used in the present invention normally contains microorganisms (bacteria, yeasts, and/or archaebacteria) that are native to the waste material. Many of these native microorganisms are capable of generating hydrogen in an anaerobic environment using the waste material as a source of nutrients. In some embodiments, the fermenting 100 step may be carried out using these native microorganisms. In some other embodiments, exogenous microorganisms capable of generating hydrogen in an anaerobic environment are introduced into the fermentation mixture. In some embodiments, both native and exogenous microorganisms capable of generating hydrogen from the waste material are used either independently or in a coordinated and/or cooperative fashion.

Suitable exogenous microorganisms may be selected for optimal hydrogen production from the waste material in the fermentation mixture and/or for their suitability for use under the fermentation conditions. It is understood by a person skilled in the art that different microorganisms may prefer or even require different waste materials for optimal hydrogen production. Given a waste material, a routine experiment may be conducted to test and identify suitable exogenous microorganisms that provide the desired level of hydrogen production and/or selectivity in anaerobic fermentation of the waste material. The present invention may thus comprise a step of selecting one or more exogenous microorganisms to enhance hydrogen production by fermenting a fermentation mixture comprising the waste material.

In some embodiments, the exogenous microorganisms may be selected from the following genera of bacteria: *Acetivibrio, Acetoanaerobium, Acetofilamentum, Acetogenium, Acetothermus, Acidaminobacter, Anaerobiospirillum, Anaerorhabdus, Anaerovibrio, Atopobium, Bacteroides, Bifidobacterium, Bilophila, Butyrivibrio, Campylobacter, Catonella, Centipeda, Dialister, Dichelobacter, Fervidobacterium, Fibrobacter, Fusobacterium, Halanaerobacter, Halanaerobium, Ilyobacter, Johnsonella, Lachnobacterium, Leptotrichia, Malonomonas, Megamonas, Mitsuokella, Oxalobacter, Pectinatus, Pelobacter, Porphyromonas, Prevotella, Propionibacterium, Propionigenium, Propionispira, Rikenella, Roseburia, Ruminobacter, Sebaldella, Selenomonas, Sporomusa, Succinimonas, Succinivibrio, Syntrophobacter, Syntrophomonas, Sutterella, Saponavida, Thermobacteroides, Thermosipho, Thermotoga, Tissierella, Wolinella, Zymophilus, Desulfobacter, Desulfobacterium, Desulfobulbus, Desulfococcus, Desulfomicrobium, Desulfomonas, Desulfomonile, Desulfonema, Desulfosarcina, Desulfotomaculum, Desulfovibrio, Desulfurella, Desulfuromonas, Thermodesulfobacterium, Acidaminococcus, Megasphaera, Syntrophococcus, Veillonella, Coprococcus, Peptococcus, Peptostreptococcus, Ruminococcus, Sarcina, Clostridium, Amoebobacter, Chromatium, Lamprobacter, Thiocapsa, Thiocystis, Thiodictyo, Thiopedia, Thiospirillum, Ectothiorhodospira, Rhodobacter, Rhodocyclus, Rhodomicrobium, Rhodopila, Rhodopseudomonas, Rhodospirillum, Erythrobacter, Methanobacterium, Methanobrevibacter, Methanococcu, Methanococcoides, Methanolobus, Methanolacinia, Methanomicrobium, Methanogenium, Methanospirillum, Methanoplanus, Methanothrix, Methanothermus, Methanocorpusculum, Methanoculleus, Methanohalobium, Methanohalophilus, Methanosarcina, Methanosphaera, Eubacterium, Abiotrophia, Atopobium, Gemella, Granulicatella, Finegoldia, Lactobacillus, Actinomyces, Arcanobacterium, Bulleidia, Collinsella, Cryptobacterium, Holdemania, Rothia, Pseudoramibacter, Mogibacterium, Slackia,* and *Eggerthella.*

In some embodiments, the fermenting step 100 is performed in a low pH environment. The present invention may use a low pH environment to enhance yield of hydrogen and/or reduce by-products such as methane. For example, methane production is typically decreased when the pH in the fermentation mixture is low, since methanogens generally are inhibited by low pH. The initial pH of the fermentation mixture in the reactor 1 may be in a range of from about 3 to about 6.5, or from about 3.5 to about 6, or from about 4 to about 5.5, or from about 4.5 to about 5. The fermenting step 100 may be conducted with or without pH control in the fermentation mixture during the fermentation. In some embodiments, the present invention may further comprise a step of maintaining the pH in the fermentation mixture during the fermentation to be about the same as its initial pH. Alternatively, the pH in the fermentation mixture may be varied during the fermentation but controlled to be in a range of from about 3 to about 6.5, or from about 3.5 to about 6, or from about 4 to about 5.5, or from about 4.5 to about 5.

The pH in the fermentation mixture may be monitored continuously or periodically. In-line or on-line monitoring techniques may be used for pH monitoring. In-line monitoring techniques use instrumentation which can be directly inserted into the reactor 1, whereas, on-line monitoring techniques involve diverting a small stream of fermentation mixture to a location where it is either continually sampled and analyzed by a fixed instrumentation, or manually sampled and tested. The stream of fermentation mixture is then either re-circulated back into the reactor 1 or taken off as waste. Examples of in-line pH monitoring instruments include, but are not limited to, glass membrane type pH electrodes, solid state type pH electrodes (e.g. silicon nitride based and metal oxide based), and optodes (optical type pH electrodes using fluorescence or absorbance measurements of pH sensitive dyes). Examples of on-line pH monitoring instruments include, but are not limited to, glass membrane type pH electrodes, solid state type pH electrodes (e.g. silicon nitride based and metal oxide based), optodes (optical type pH electrodes using fluorescence or absorbance measurements of pH sensitive dyes), and flow injection analysis (FIA).

The pH in the fermentation mixture, as measured by the in-line or on-line monitoring techniques, may be used for adjusting the pH in the fermentation mixture to thereby maintain an optimal or desirable pH during the fermentation. The pH in the fermentation mixture may be adjusted by addition of deoxygenated solutions of a base such as sodium hydroxide to increase the pH, and/or addition of deoxygenated solutions of an acid such as hydrochloric acid to decrease the pH. This pH adjustment may be performed manually, or may be automated.

The temperature in the reactor 1 is maintained at a temperature that is suitable for the microorganisms (native and exogenous) in the fermentation mixture to grow and produce hydrogen. For example, the temperature may be from about 25° C. to about 40° C., or from about 27° C. to about 38° C., or from about 29° C. to about 37° C., or from about 31° C. to about 37° C., or from about 33° C. to about 37° C., or from about 35° C. to about 37° C. The temperature in the reactor 1 may be controlled manually or in an automated fashion.

In some embodiments, a suitable nitrogen source may be added to the fermentation mixture to enhance the growth of the microorganisms, as well as enhance the yield and/or selectivity of hydrogen production. Some waste materials may be low in nitrogenous nutrients, thus not optimal to fully support the growth of hydrogen producing microorganisms in the fermentation mixture. By adding a nitrogen source, the amount of nitrogen in the fermentation mixture may be adjusted to be in a range of from about 0.01 wt. % to about 10 wt. %, or from about 0.05 wt. % to about 9 wt. %, or from about 1 wt. % to about 8 wt. %, or from about 2 wt. % to about 7 wt. %, or from about 3 wt. % to about 6 wt. %, or from about 4 wt. % to about 5 wt. % of the mixture. Alternatively, the amount of nitrogen in the fermentation mixture may be in a range such as about 0.01 wt. %-0.5 wt. %, about 0.5 wt. %-1 wt. %, about 1 wt. %-2 wt. %, about 2 wt. %-3 wt. %, about 3 wt. %, about 3 wt. %-4 wt. %, about 4 wt. %-5 wt. %, about 5-6 wt. %, about 6-7 wt. %, about 7 wt. %-8 wt. %, about 8 wt. %-9 wt. %, or about 9 wt. %-10 wt. % of the mixture.

In some embodiments, one or more vitamins may be added to the fermentation mixture to enhance the growth of the microorganisms, as well as enhance the yield and/or selectivity of hydrogen production. Some of the vitamins that may be added include thiamine, cobalamine, riboflavine, niacinamide, pantothenic acid, biotin, ascorbic acid, retinol, procalciol, tocopherol, folic acid and pyridoxamine. In some embodiments, the amount of vitamins in the fermentation mixture is adjusted to a final concentration of at least about 19 mg/L, or from about 19 to about 94 mg/L, or from about 50 to about 94 mg/L in the fermentation mixture.

In some embodiments, one or more essential trace elements may be added to the fermentation mixture to enhance the growth of the microorganisms, as well as enhance the yield and/or selectivity of hydrogen production. Some of the essential elements may be vitamins that may be Mn, Fe, Ni, Cu, Zn, Co, Se, Mo, V, W.

In some embodiments, the waste material may be pretreated before the fermenting step 100. The pretreatment can prepare certain waste materials to be more effectively utilized by the microorganisms during the fermentation process. For example, pretreatment may increase solubility for some components in the waste material. Pretreatment may also help to break some macromolecules in the waste material to medium or small molecules that are more soluble and thus efficiently metabolized by the microorganisms in the fermentation mixture. Pretreatment may also remove some components in the waste material that inhibit hydrogen production or are harmful to the hydrogen producing microorganisms.

Examples of pretreatment techniques include a heat treatment, an acid treatment, an alkali treatment and combinations thereof. In some embodiments the heat treatment is for a period of from about 10 minutes to about 60 minutes, or from about 15 minutes to about 50 minutes, or from about 20 minutes to about 45 minutes, or from about 25 minutes to about 40 minutes, or from about 25 minutes to about 35 minutes. The temperature for the heat treatment may be from about 60° C. to about 150° C., or from about 70° C. to about 130° C., or from about 75° C. to about 120° C., or from about 80° C. to about 110° C., or from about 80° C. to about 105° C., or from about 80° C. to about 100° C. In some embodiment, when the temperature of the heat treatment is near or above 100° C., pressurization of the waste material may be required.

In some embodiments, the acid treatment is for a period of from about 12 hours to about 36 hours, or from about 15 hours to about 33 hours, or from about 17 hours to about 30 hours, or from about 20 hours to about 28 hours, or from about 22 hours to about 25 hours. The pH for the acid treatment may be from about 0.1 to about 3, or from about 0.3 to about 2.5, or from about 0.5 to about 2. In some embodiments, the alkali treatment is for a period of from about 12 hours to about 20 hours, or from about 13 hours to about 19 hours, or from about 14 hours to about 18 hours, or from about 15 hours to about 17 hours, or from about 15 hours to about 16 hours. The pH for the alkali treatment may be from about 12 to about 14, or from about 12.5 to about 13.5, or from about 12.7 to about 13.3.

Anaerobic fermentation allows the microorganisms in the fermentation mixture to metabolize the organic compounds in the waste material as nutrients, which usually leads to growth of the microorganism population. In some embodiments, the fermentation conditions may result in maintenance of the population of microorganisms at substantially the same level throughout the fermentation. The organic compounds in the waste material are metabolized by the microorganisms to provide building blocks and metabolic energy for the microorganisms. In some embodiments, the organic compounds in the fermentation mixture are the sole source of the metabolic energy and no light is present for providing additional energy. This type of anaerobic fermentation is called "dark fermentation." In some embodiments, light is present in the reactor 1 for providing some metabolic energy to the microorganisms, this type of anaerobic fermentation is called "light fermentation." The metabolism of the organic compounds generates electrons that need to be disposed of in order to maintain electrical neutrality. In aerobic environments, oxygen acts as an electron acceptor and is reduced to water. In anaerobic environments, no oxygen is present. Often protons accept electrons and are thereby reduced to hydrogen ($H_2$).

Therefore, in an anaerobic environment, metabolism of organic compounds by the microorganisms produces hydrogen at the fermenting step 100. Other products from the fermenting step 100 may include methane, carbon dioxide and organic acids such as formic acid, valeric acid, acetic acid, butryric acid, propionic acid, and lactic acid. The present invention provides a method that enhances hydrogen production, while suppressing the production of other products, especially methane. For example, the organic acids produced during the fermentation process can help to keep the pH low in the fermentation mixture. As described herein, a low pH in the fermentation mixture may inhibit methane production, and thus may be employed to enhance the yield and/or selectivity of hydrogen production.

Figure 2:
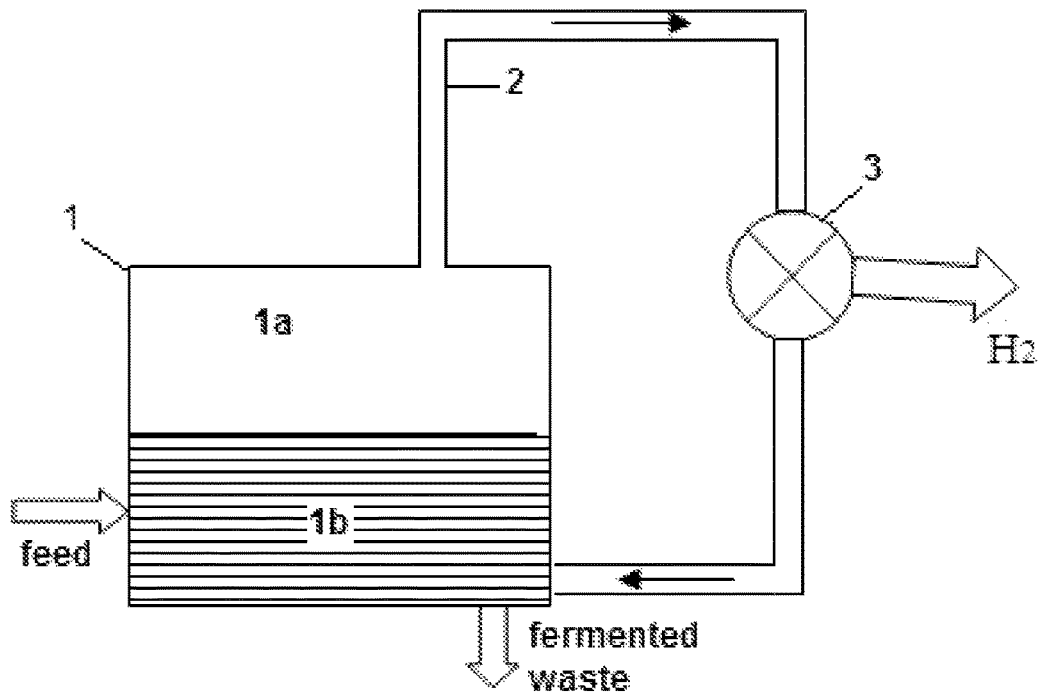
FIG. 2 represents an apparatus for generating hydrogen from a fermentation mixture comprising a waste material, according to one embodiment of the present invention.

The fermenting step 100 is performed in a reactor 1, which is a sealed container with a liquid portion 1b and a headspace 1a (FIG. 2). The fermentation mixture is the liquid portion 1b while the produced gas is located in the headspace 1a. The reactor 1 is not limited to any particular reactor design, but may be any sealable reaction vessel that can tolerate the temperature and pH required for the present invention.

In some embodiments, the fermentation mixture in the reactor 1 is continuously or periodically agitated. The dissolved hydrogen in the liquid portion 1b can be reduced significantly by agitation, which reduces inhibition of further hydrogen production by the dissolved hydrogen. In addition, agitation also creates a more homogenous fermentation mixture with the microorganisms in more intimate contact with the waste material.

In the method of the invention, hydrogen gas is separated from the gas in the headspace 1 of the reactor ("headspace gas") to provide hydrogen and a remainder gas containing the non-hydrogen components of the headspace gas. The remainder gas obtained after hydrogen separation/removal is recirculated 301 back to the reactor 1 (FIG. 2). The recirculated remainder gas can function as an agitation mechanism. For example, the recirculated remainder gas may enter at or near the bottom of the reactor 1 and bubble through the fermentation mixture in order to agitate the fermentation mixture and encourage the release of dissolved hydrogen into the headspace gas.

In some embodiments, the reactor 1 may also include a mechanical means to agitate the fermentation mixture. The agitation may be carried mechanically at a rotation speed in the range of from about 10 to about 60 rpm, or from about 15 to about 55 rpm, or from about 20 to about 50 rpm, or from about 25 to about 45 rpm, or from about 30 to about 40 rpm.

The fermentation mixture, comprising mixed waste material and microorganisms, is placed in the reactor 1 to permit fermentation by the microorganisms to produce hydrogen. Fermentation can be conducted in a batch mode, a fed-batch mode, or a continuous mode. A standard batch fermentation uses a closed system in which the composition of the fermentation mixture is established at the beginning of the fermenting step 100 and not subjected to artificial alterations during the fermentation. Therefore, at the beginning of the fermentation, the fermentation mixture is mixed with the microorganisms, and the fermentation is permitted to occur without anything being added to or retrieved from the fermentation mixture during the fermentation. However, the batch fermentation still permits addition of chemicals for adjusting pH of the fermentation mixture, removal of gas from the headspace 1a and recirculation of remainder gas back to the headspace 1a.

A modified version of the standard batch fermentation is a fed-batch fermentation. A fed-batch fermentation is identical to a standard batch fermentation except that a growth-limiting substrate is incrementally added as the fermentation progresses. A fed-batch fermentation is useful in various circumstances, such as when catabolite repression is apt to inhibit metabolic action in the cells or where it is desirable to have limited amounts of substrate in the medium, for example to control the reaction rate. Batch and fed-batch fermentations are common and well known in the art (Thomas D. Brock in Biotechnology: A Textbook of Industrial Microbiology, Second Edition (1989) Sinauer Associates, Inc., Sunderland, Mass., or Desphande and Mukund, *Appl. Biochem. Biotechnol.*, vol. 36, pages 227-234, 1992).

The fermentation may also be a continuous fermentation. A continuous fermentation is carried out in a flowing system in which fresh fermentation mixture or at least one of its components is added continuously to the reactor 1 and an equal amount of fermented mixture is removed simultaneously from the reactor 1. Continuous fermentation permits microorganism cells to be maintained at a constant high density where the cells are mainly in a continuous growth mode. In a continuos fermentation, the biomass in the removed fermentation mixture may be recycled back to the reactor 1 for further fermentation.

Continuous fermentation allows modulation of one or more factors that affect microorganism growth and/or yield/selectivity hydrogen production. For example, continuous fermentation allows maintaining a limiting nutrient such as the carbon source or nitrogen level at a fixed concentration while letting all other parameters to vary. In another example, a number of factors affecting microorganism growth can be altered continuously while the microorganism cell concentration is kept constant or substantially. Continuous fermentation strives to maintain steady-state growth conditions and thus the cell loss due to the fermentation mixture being drawn off the reactor 1 must be balanced against the cell growth rate during the fermentation process. Methods of modulating nutrients and factors for continuous fermentation, as well as techniques for maximizing the rate of cell duplication, are well known in the art of industrial microbiology and a variety of methods are detailed in the textbook (Thomas D. Brock, Biotechnology: A Textbook of Industrial Microbiology, Second Edition, Sinauer Associates, Inc., Sunderland, Mass. (1989)).

The gas produced at the fermenting step 100, including hydrogen, is released to headspace 1a of the reactor 1. If the hydrogen in the headspace 1a accumulates to a high partial pressure, hydrogen production by the microorganisms is inhibited, because hydrogen production is sensitive to hydrogen concentration in the reactor and is thus subject to end-product inhibition. As the hydrogen concentration increases in the headspace 1a, hydrogen production decreases and the metabolic balance shifts to production of other chemicals such as organic acids, ethanol, acetone, butanol, and/or methane. The present invention reduce the hydrogen partial pressure in the headspace 1a, thus keeping the hydrogen partial pressure, which reflects the hydrogen concentration in the headspace gas, at a relatively low level in order to enhance yield and/or selectivity of hydrogen production by suppressing or eliminating end-product inhibition which would otherwise be caused by the presence of significant amounts of hydrogen in the headspace gas. This may be achieved by separating 200 hydrogen from non-hydrogen components of a headspace gas of the reactor during the fermentation to produce a remainder gas and the fermentation may be continued 300 with at least a portion of the non-hydrogen components of the remainder gas from which the hydrogen was separated, located in the reactor. In another embodiment, the reduction of hydrogen partial pressure may be achieved by removing 201 hydrogen from a gas generated in a headspace of the reactor during fermentation to produce a remainder gas and recirculating 301 at least a portion of the remainder gas back to the headspace.

In some embodiments, the present invention further comprises a step of monitoring the hydrogen partial pressure and thus the hydrogen concentration in the headspace 1a to determine whether the hydrogen partial pressure exceeds a predetermined level at which hydrogen should be removed from the headspace 1a. The hydrogen partial pressure in the headspace 1a may be monitored continuously or periodically. Measurement of hydrogen partial pressure may be carried out using techniques known in the art, and may be carried out in the headspace 1a or externally in a fluid communication system 2 used to remove gas from the reactor 1. Methods for determining hydrogen partial pressure in a gas may include the use of fiber optic sensors based on the chemochromic reaction of certain transition metal oxides, such as tungsten oxide ($WO_3$) with hydrogen in air, catalyzed by palladium or platinum. The color change of the film in the presence of hydrogen may be detected by reflectance spectroscopy. Another method for determining hydrogen partial pressure employs thermal conductivity detectors (TCD), which monitor the thermal conductivity of the gas in the headspace 1a and compare it to that of a reference gas. The difference in conductivity can then be calibrated to a hydrogen concentration. Thermal conductivity detection may also be used in conjunction with gas chromatography (GC) to identify the various components of the gas in the headspace 1a and obtain their respective concentrations and/or partial pressures. GC may also be used in combination with TCD for determining the hydrogen partial pressure in a gas. Other methods for determining hydrogen partial pressure in a gas include gas sensing based on resistance changes upon hydrogen adsorption on platinum and/or palladium, and field effect transistors based on carbon nanotubes. The hydrogen partial pressure information thus obtained may be used for feedback control of the removal of hydrogen from the headspace 1a of the reactor 1.

The present invention includes a hydrogen removal device 3. In some embodiments, the hydrogen removal device may receive the headspace gas via the fluid communication system 2. In other embodiments, the hydrogen removal device 3 may be located in headspace 1a or at an outlet of the reactor 1. The hydrogen in the headspace gas may be specifically separated 200 from the headspace gas. The remainder gas after the hydrogen separated can remain in the headspace during continuous fermentation.

The hydrogen removal device 3 removes hydrogen from the gas to produce hydrogen gas and a remainder gas. At least portion of the remainder gas is recirculated 301 back to the headspace 1a. Recirculation may be accomplished via the fluid communication system 2 when hydrogen removal device 3 is located external to headspace 1a. Return of the remainder gas to headspace 1a may be employed to maintain the partial pressure of non-hydrogen components of the headspace gas, such as, for example, carbon dioxide, carbon monoxide and methane, at certain minimum levels in headspace 1a in order to inhibit production of these non-hydrogen components in the headspace gas. Thus, the fermentation process of the present invention will preferentially produce hydrogen, by enhancing the yield and/or selectivity of hydrogen production in the process.

The hydrogen removal device 3 may be manually controlled, or may be automatically triggered based on the hydrogen partial pressure in the headspace 1a, preferably using a computer-based control system. In one embodiment, when the hydrogen partial pressure in the headspace 1a reaches a threshold or above, the hydrogen removal device 3 is automatically activated by the control system to begin removing 201 hydrogen from the headspace 1a. In one embodiment, the hydrogen removal device 3 may be continuously operated to remove 201 hydrogen from the headspace 1a on a continuous basis.

In some embodiments, the hydrogen removal device 3 comprises a pump to facilitate gas retrieval from the headspace 1a and recirculation 301 of remainder gas back to the headspace 1a. Alternatively or additionally, in some embodiments, a pump may be included in the fluid communication system 2 to create a gas flow in the fluid communication system 2 and through the hydrogen removal device 3.

The hydrogen removal device 3 removes hydrogen from the gas retrieved from the headspace 1a to provide a hydrogen stream and a remainder gas containing non-hydrogen components (FIG. 2). The hydrogen removal device 3 may employ any mechanisms known to a person skilled in the art that is capable of separating hydrogen from a gas. In some embodiments, the hydrogen removal device 3 may comprise a molecular sieve, an adsorbent or a selective membrane for hydrogen removal.

A molecular sieve is a material with very small holes of precise and uniform size. These holes are small enough to block large molecules while allowing small molecules to pass. Hydrogen molecules are smaller than other components in the gas, such as carbon dioxide, carbon monoxide, and methane. The molecular sieve of the present invention will have sufficiently small holes to only permit hydrogen molecules to pass through and thereby be separated from the non-hydrogen components in the headspace gas. At least some, or preferably all, o the non-hydrogen components making up the remainder gas are recirculated to the headspace 1a. The molecular sieve may be made from zeolites, active carbon, porous glass, and clays such as montmorillonite intermixes. The holes of the molecular sieve preferably have a size of less than about 10 angstroms, or less than about 8 angstroms, or less than about 5 angstroms, or less than about 3 angstroms. For example, a suitable carbon molecular sieve is described in WO 2011/084994 which is hereby incorporated herein by reference.

The adsorbent in the hydrogen removal device 3 can selectively absorb hydrogen from the headspace gas. The adsorbent is capable of absorbing hydrogen and releasing the absorbed hydrogen without significantly altering the properties of the adsorbents. The adsorbent with absorbed hydrogen can then be retrieved from the hydrogen removal device 3 to release the absorbed hydrogen, preferably in a hydrogen container, and then replaced back into the hydrogen removal device 3. Thus, the adsorbent may be cycled between the hydrogen removal device 3 and a hydrogen container.

Adsorbents of the present invention can be divided into physisorption adsorbents and chemisorption adsorbents, depending on the mechanism of hydrogen absorption by the absorbents. The physisorption adsorbents may be made from metal-organic frameworks, porous carbons, zeolites, clathrates, and organic polymers.

In chemisorption adsorbents, hydrogen is chemically bonded to the adsorbents to form a monolayer of hydrogen on the surface of the absorbents. The chemisorption adsorbents may be made from interstitial metal hydrides (such as $LaN_{i5}Hx$), covalently bound metal hydrides (such as $Mg_{H2}$, $Al_{H3}$, $LiB_{H4}$, $NaB_{H4}$, $Mg(B_{H4)2}$, $LiN_{H2}$, and $Mg(N_{H2)2}$), metal amides, borohydrides, hydrocarbons, ammonia borane, and alane.

In one embodiment, the adsorbents are made from a metal-organic material, which is a crystalline material consisting of metal ions linked together by organic ligands which generate micropores and channels. Since the metal-organic material is synthesized from metal ions and organic building blocks, the topology, pore size, and surface area of such metal-organic absorbents can be tuned by, for example, selection of the starting metal ions and organic building blocks, as well as the ratios between them.

In another embodiment, the adsorbents are made from metal hydrides. Metal hydrides may be produced in the form of liquids, solid membranes and pellets at ambient temperature and pressure. The adsorbents preferably have pore sizes of less than about 10 angstroms, or less than 8 angstroms, or less than 5 angstroms, or less than 2 angstroms.

Examples of hydrogen adsorbents have been described previously (Huang et al., "Hydrogen adsorption on modified activated carbon," *International Journal of Hydrogen Energy*, vol. 35, pages 2777-2780, 2010; Miller, "The adsorption of gases on solids," Cambridge University Press, 2013; Nugent et al., "Porous materials with optimal adsorption thermodynamics and kinetics for $CO_2$ separation," *Nature*, vol. 495, pages 80-84, 2013; Suh et al., Hydrogen storage in metal-organic frameworks," *Chemical reviews*, vol. 112, pages 782-835, 2011, the disclosure of which is hereby incorporated by reference herein).

Selective membranes may also be used in the hydrogen removal device 3 to remove 200 hydrogen from the headspace gas. Selective membranes for hydrogen separation have been discussed previously (U.S. Pat. Nos. 6,159,272; 6,011,192; 5,082,481; 5,447,549; 7,211,706, Carta et al., "An efficient polymer molecular sieve for membrane gas separations," *Science*, vol. 339, pages 303-307, 2013; Du et al., "Separation of hydrogen and nitrogen gases with porous graphene membrane," *The Journal of Physical Chemistry C*, vol. 115, pages 23261-23266, 2011; Li et al., "Molecular sieve membrane: supported metal-organic framework with high hydrogen selectivity," *Angewandte Chemie*, vol. 122, pages 558-561, 2010, each of which are hereby incorporated by reference herein).

In one embodiment, the selective membrane is a carbon molecular sieve membrane. For example, a polymer could be pyrolyzed onto a porous support capable of withstanding high temperatures. Hydrogen molecules permeate through the membrane to the permeate/downstream side and the rejected components (remainder gas now substantially depleted in hydrogen) remain on the high pressure retentate/reject side. The carbon molecular sieve membrane preferably has a high $H_2/CH_4$ selectivity (>50) and high permeance (>500 GPU Gas Permeation Unit, $1 \times 10^{-6}$ $cm^3 STP/cm^2 \cdot sec \cdot cmHg$). This combination of the permeance and selectivity of the carbon molecular sieve membrane allows hydrogen recovery to be tuned by changing the membrane area and/or feed/permeate pressure ratio. Carbon molecular sieve membranes are typically prepared by carbonizing thermosetting polymer precursors at high temperatures ranging from 400-1000° C. See Hagg et al., "The Recovery by Carbon Molecular Sieve Membranes of Hydrogen Transmitted in Natural Gas Networks," *International Journal of Hydrogen Energy*, vol. 33, pages 2379-2388, 2008; and Saufi et al., "Fabrication of Carbon Membranes for Gas Separation—A review," *Carbon*, vol. 42, pages 241-259, 2004, the disclosure of which is hereby incorporated by reference herein.

The selective membrane may also be a ceramic membrane, such as the one described in U.S. Pat. No. 5,611,931, the disclosure of which is hereby incorporated by reference herein), provided with porous ceramic tubes permeable to hydrogen. The selective membrane may also be a metal membrane as described in U.S. Pat. No. 6,649,559, the disclosure of which is hereby incorporated by reference herein.

In some embodiments, carbon dioxide in the headspace 1a may also be removed. Removal of carbon dioxide may increase hydrogen production, as described in Park, et al., "Removal of Headspace $CO_2$ Increases Biological Hydrogen Production," *Environ. Sci. Technol.*, vol. 39, pages 4416-4420, 2005. In addition, removal of carbon dioxide from the gas will reduce greenhouse gas emission. Removal of carbon dioxide may be achieved by use of devices known to a person skilled in the art. WO 2009/070273 describes many types of carbon dioxide scrubbers that may also be used in the present invention, the disclosure of which is hereby incorporated by reference herein.

The remainder gas from the hydrogen removal device 3, after removal of hydrogen and optionally carbon dioxide, is at least partially recirculated 300 back to the headspace 1a. The invention is capable of keeping the hydrogen partial pressure in the headspace 1a low and the partial pressures for other gaseous components in the headspace 1a relatively high, in order to provide an enhanced yield and/or selectivity for production of hydrogen.

In some embodiments, non-gaseous chemical products of the fermenting step 100 may also be recovered from the fermented mixture by reverse osmosis or filtration, depending on the characteristics of the non-gaseous chemical products. The filtration may be dead-end filtration, cross-flow filtration, or ultrafiltration, which are well-known techniques in the art. Filtration membranes can be polymeric or ceramic, depending upon the application.

Dead-end filtration, also known as normal-flow filtration, requires feed to pass through a filter membrane or bed, the solids being trapped in the filter and the filtrate being released at the other end. Because the filter is less subject to clogging, cross-flow filtration is more suitable for use in a continuous process.

In another aspect, the present invention provides a fermentation apparatus for producing hydrogen, comprising a reactor 1 suitable for anaerobic fermentation having a headspace 1a, a hydrogen removal device 3 to remove hydrogen from the headspace gas and provide a remainder gas of substantially non-hydrogen components, a fluid communication system 2 in communication with the reactor 1 and the hydrogen removal device 3 for retrieving headspace gas from the headspace 1a, transporting the headspace gas to the hydrogen removal device 3, and recirculating at least a portion of the remainder gas from the hydrogen removal device 3 to the headspace 1a. The hydrogen removal device 3 is capable of selectively removing 200 hydrogen from the headspace gas of the reactor 1.

The recirculated remainder gas preferably enters at or near the bottom of the reactor 1, thus causing agitation to the fermentation mixture in the reactor 1. A pump for generating a gas flow in the fluid communication system 2 may be part of the hydrogen removal device 3 or part of the fluid communication system 2 (FIG. 2).

The hydrogen removal device 3 comprises an element selected from a molecular sieve, an adsorbent, and a selective membrane, for separating hydrogen from the other components of the headspace gas, as described herein. In some embodiments, the reactor 1 comprises a mechanical means for agitating the fermentation mixture in the reactor 1. Agitation of the fermentation mixture may accelerate release of hydrogen from the fermentation mixture into the headspace 1a.

In some embodiments, the fermentation apparatus comprises a carbon dioxide removal device for removing carbon dioxide from the headspace gas. The carbon dioxide removal device may be implemented as, for example, a carbon dioxide scrubber, where the headspace gas passes through the carbon dioxide scrubber for carbon dioxide removal.

In some embodiments, the fermentation apparatus comprises a control system for monitoring and adjusting anaerobic fermentation parameters. The control system may include one or more sensors for measuring one or more of the temperature in the reactor 1, the pH in the fermentation mixture, the hydrogen partial pressure in the headspace 1a, and the velocity of the gas flow in the fluid communication system 2. Based on the readings from the sensors, the control system may automatically adjust the fermentation parameters to ensure optimal production of hydrogen. For example, the control system may be used to implement pH control in the fermentation mixture as discussed above, to provide a suitable temperature in the reactor 1 and to adjust conditions to ensure a low hydrogen partial pressure in the headspace 1a. In one embodiment, when the hydrogen partial pressure in the headspace 1a is at or above a threshold pressure, the gas in the headspace 1a may be automatically transferred to the hydrogen removal device 3, where hydrogen is selectively removed and at least a portion of the remainder gas containing substantially all non-hydrogen components are recirculated 300 back to the headspace 1a.

The following examples are illustrative, but not limiting, of the methods and compositions of the present disclosure. Other suitable modifications and adaptations of the variety of conditions and parameters normally encountered in the field, and which are obvious to those skilled in the art, are within the scope of the disclosure.

EXAMPLES

Equipment Used in Examples

Storage Tanks (D-101, D-102)

The storage tanks were used to store separately both food sludge (with 14% solids) and wastewater sludge (with 3.5% solids). A jet-mixing pump (e.g., P-101 or P102) was used to ensure that the sludge within each storage tank was well mixed. The jet-mixing pumps removed sludge from the top portion of tank and fed it back into the bottom portion of the tank to ensure that the solid components in the sludge did not settle to the bottom of the tank. The total volume of each elliptical tank was 189,271 liters (50,000 gal) with a height of 52.07 cm (20.5') and a diameter of 52.07 cm (20.5'). The tanks were kept at a temperature of 20° C. (68° F.) and at a pressure of 1.01 Bar (14.7 psig) (atmospheric pressure).

Pumps (P-101, P-102, P-103, P-104)

P-101 and P-102 were similar pumps that were used for jet-mixing the components in the storage tanks. These pumps were designed to have a flow rate of 1703.4 liter/min (450 gal/min) at 14.9 kW (20 hydraulic horsepower). The reason for the high design flow rate is to ensure a well-mixed sludge for supply to the hydrogen production process.

P-103 and P-104 were both centrifugal pumps but each had a different design to produce a different flow rate. As both sludge feeds were mostly composed of water, a constant density of 1000.033 Kg/m$^3$ (62.43 lb/ft$^3$) and viscosity of water were assumed for both sludge feeds. The calculated volumetric flow rates of the pumps were 45.425 liter/min (12 gal/min) and 60.945 liter/min (16.1 gal/min) for pumps P-103 and P-104, respectively. The power required for these two pumps was 2.98 kW (4 hydraulic horsepower) and 3.73 kW (5 hydraulic horsepower) for pumps P-103 and P-104, respectively.

Mixer (M-101)

An inline mixer was used to mix both food and wastewater sludge to achieve the desired solids percentage. A total of 45.425 liter/min (12 gal/min) of food sludge and 60.945 liter/min (16.1 gal/min) of wastewater sludge were pumped into the inline mixer and mixed before being heated by passage through a spiral heat exchanger (inline mixer model DS-425, Admix).

The axial and radial tip speed of the mixer were 1,051.56 meter/minute (3450 fpm) and 1,651.711 2 meter/minute (5419 fpm), respectively. The motor size of the inline mixer was 14.9 kW (20 HP) with a motor speed of 3600 rpm. The maximum flow rate of the inline mixer was 662.45 liter/min (175 gpm).

Spiral Heat Exchanger (E-101)

The spiral heat exchanger was a double pipe heat exchanger with a counter-current flow. The source of heat for this heat exchanger was water at a temperature of 60° C. (140° F.) with a condensate temperature of 26.7° C. (80° F.). The amount of energy consumed by the heat exchanger was 4.689 kW (16000 BTU/hr). The spiral heat exchanger had a low installation cost and worked efficiently.

Reactor (R-201)

The anaerobic reactor was a continuously stirred tank reactor known as a CSTR. A hydraulic residence time of 17 hours was designed by using a volume of the CSTR at 113562 liters (30000 gal) based on a volumetric flow rate of 105.99 liter/min (28 gal/min) in and out of the reactor. The footprint of the CSTR was designed with a diameter of 34.67 cm (13.65') and a height of 69.34 cm (27.3').

To further optimize the anaerobic digestion, the reactor was maintained at a temperature of 36.7° C. (98° F.) and a pressure of 1.01 Bar (14.7 psi). A pressure valve was placed on top of the reactor to allow gas release when the headspace of the reactor was filled with produced gases.

Pumps (P-201)

P-201 was a centrifugal pump designed to pump a mixture of solids and liquid through a filtration unit (D-201). The calculated mass flow rate of the pump was 106.12 kg/min (233.95 lb/min). The pump had a power of 3.728 kW (5 HP) with an output pressure of 6.2 bar (90 psig). The high output pressure allowed solids and liquids to pass through the sludge filter unit (D-201) with ease.

Sludge Filter (D-201)

The sludge filtration unit was an important unit to separate a portion of the solids from the liquids (acid and water), to allow further distillation of the acid and recycling of the saturated solids. The filtration unit worked as a cross-flow filtration, which permitted the solids to pass through the system for recycling and the water/acid to pass in a cross-flow direction. The ultrafiltration unit had three outlets with one specifically for the acid. Two other outlets were for the waste solid/liquid stream and the solid stream, both of which were recycled back into the reactor.

Iron Sponge Vessel (D-301)

An iron sponge vessel was used for removal of hydrogen sulfide from a gaseous mixture. The vessel was made of a stainless steel box with an iron sponge bed to ease the handling of the iron sponge and to prevent corrosion. A down-flow gas was recommended to maintain the moisture in the vessel with a contact time of one minute. To enhance the reaction kinetics of iron oxide to hydrogen sulfide and water, the temperature in the vessel was kept at 36.7° C. (98° F.). The pressure in the vessel was kept at 1.01 Bar (14.7 psig). The vessel had a size of 152.4 cm (5 ft) in height and 91.44 cm (3 ft) in diameter. The iron sponge has a removal rate of 2500 mg $H_2S$/g $Fe_2SO_3$. The amount of iron sponge required in a year was projected to be 4594.4 kg (10.129 lb).

Palladium-Silver Membrane (SP-301)

To separate hydrogen gas from other organic gases, a palladium-silver membrane with 77 wt. % Pd and 23 wt. % Ag was used. The membrane allowed high purity hydrogen to be permeated. The temperature of the membrane was kept below 450° C. (842° F.) to maximize the hydrogen purity. The minimum flux allocation to the membrane was 10 L/min.

Hydrogen Compressor (C-301)

A hydrogen compressor C-301 was used to compress purified hydrogen for storage at a pressure of 206.84 bar (3000 psig). The compressor was sold by Sundyne and had a power of 1.118 kW (1.5 HP) and a maximum displacement of 4.814 liter/min (0.17 ft$^3$/min). The temperature of the hydrogen compressor was maintained at 468.52° C. (875.33° F.).

Example 1

A food sludge (with 14% solids) was stored in storage tank D-101 at 20° C. (68° F.) with a jet-mixing pump P-101 that continuously circulated the content of the tank. The purpose of the jet-mixing pump was to prevent sedimentation of the solids at the bottom of the vessel. The flow rate out of D-101 was 45.359 kg/min (100 lb/min), with the output being pumped through a centrifugal pump. Storage tank D-102, containing wastewater sludge (with 3.5% solids), was likewise continuously jet-mixed. The wastewater sludge was pumped at a flow rate of 60.92 kg/min (134.3 lb/min) by the jet-mixing pump P-102 to accommodate the target of 106 liter/min (28 gal/min). Outputs from both storage tanks were mixed with an inline mixer, M-101, where the sludge was ground and mixed to obtain a feed sludge with 8% solids.

The food sludge had a pH 7.7 with an alkalinity of 3720 mg/L, volatile solids of 10550 mg/L, total solids of 12650 mg/L, and a soluble chemical oxygen demand of 383 mg/L with a total chemical oxygen demand of 10050 mg/L. The wastewater sludge had a pH 4.6 with an alkalinity of 0.3 mg/L, volatile solids of 129300 mg/L, total solids of 183530 mg/L, and a soluble chemical oxygen demand of 84280 mg/L with a total chemical oxygen demand of 164670 mg/L.

The feed sludge (with 8% solids) was pumped into an inline heat exchanger, E-101 at a rate of 106.3 kg/min (234.3 lb/min) and a pressure of 4.83 bar (70 psig). In E-101 the feed sludge was heated to a temperature of 36.7° C. (98° F.). The feed sludge then flowed along an inclination into an anaerobic reactor R-201 at a rate of 106.3 kg/min (234.4 lb/min), at a temperature of 36.7° C. (98° F.) and atmospheric pressure.

Example 2

The feed sludge had a residence time of 17 hours in the anaerobic reactor while assuming that the reactor R-201 was operated at steady state with a 95% solid recycle. The total solids retention time for the reactor was 20 days. The gases in the headspace of the reactor were actively removed during the fermentation process at a rate of 50 g/min (0.11 lb/min).

The reacted sludge, which consisted of organic acids, unreacted compounds and other inert materials, flowed out from the bottom of the reactor at a rate of 134.44 kg/min (296.4 lb/min) and at 36.7° C. (98° F.). The reacted sludge was then pumped into a membrane separator D-201 at a pressure of 6.2 bar (90 psig). The membrane separator D-201 separated the reacted sludge into three streams: a first stream with dry solids as a waste stream at a flow rate of 0.425 kg/min (0.937 lb/min), a second stream that was directly recycled back into the reactor at a flow rate of 28.3 kg/min (62.4 lb/min), a temperature of 36.7° C. (98° F.) and a pressure of 1.01 bar (14.7 psi), and a third stream that was an aqueous solution of organic acids at a flow rate of 105.85 kg/min (233.36 lb/min), a temperature of 36.7° C. (98° F.) and a pressure of 1.01 bar (14.7 psi). The second stream contained about 28% solids and some organic acids.

Example 3

The gases in the headspace of the reactor R-201 were pumped through a hydrogen sulfide removal tank, D-301 that was operated at a temperature of 36.7° C. (98° F.) and a pressure of 1.014 bar (14.7 psi). The hydrogen sulfide removal tank contained an iron oxide sponge to trap the hydrogen sulfide, while allowing the other organic gases and hydrogen gas to pass through it. After the hydrogen sulfide was successfully removed, the remaining gases were then passed through compressor C-301, which compressed the gases to a pressure of 20.7 bar (300 psi) and at a temperature of 228.71° C. (443.67° F.). The compressed gases flowed into a silver/palladium membrane separator SP-301, which separated hydrogen from other organic gases. The separated, highly concentrated hydrogen was obtained from the separator SP-301 at a rate of 26.3 g/min (0.058 lb/min). The highly concentrated hydrogen was then compressed in diaphragm compressor C-302 under a pressure of 206.89 bar (3000 psi) and at a temperature of 468.52° C. (875.33° F.). The compressed hydrogen gas was then cooled and stored in tank D-302.

The other components in the gases included carbon dioxide, methane, acetate and butyric acid. The acetate and butyric acid may be condensed to a liquid for further use. The carbon dioxide may be released into the atmosphere or stored for further use.

The aqueous solution of organic acids produced by the membrane separator D-201 (the third stream) was fed to a distillation column T-301 at a rate of 105.83 kg/min (233.34 lb/min) for purification of the organic acids and acetates. Some species of the organic acids included propionic acid, long chain fatty acids, acetic acid, and butyric acid.

Example 4

This example is the same as Example 1, except that the feed sludge was heated to a temperature of 36.7° C. (98° F.) by a jacketed vessel with a volume of 189270.59 liters (50,000 gallons), instead of using a spiral heat exchanger.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A method of producing hydrogen from a waste material, comprising steps of:
   a) fermenting a fermentation mixture comprising the waste material in a reactor with a headspace under anaerobic conditions;
   b) removing hydrogen from a gas generated in the headspace during fermentation to provide hydrogen and a remainder gas; and
   c) recirculating at least a portion of the remainder gas to the reactor.

2. The method of claim 1, further comprising a step of introducing at least one microorganism into the fermentation mixture.

3. The method of claim 2, wherein the at least one microorganism is selected from the bacteria genera *Acetivibrio, Acetoanaerobium, Acetofilamentum, Acetogenium, Acetothermus, Acidaminobacter, Anaerobiospirillum, Anaerorhabdus, Anaerovibrio, Atopobium, Bacteroides, Bifidobacterium, Bilophila, Butyrivibrio, Campylobacter, Catonella, Centipeda, Dialister, Dichelobacter, Fervidobacterium, Fibrobacter, Fusobacterium, Halanaerobacter, Halanaerobium, Ilyobacter, Johnsonella, Lachnobacterium, Leptotrichia, Malonomonas, Megamonas, Mitsuokella, Oxalobacter, Pectinatus, Pelobacter, Porphyromonas, Prevotella, Propionibacterium, Propionigenium, Propionispira, Rikenella, Roseburia, Ruminobacter, Sebaldella, Selenomonas, Sporomusa, Succinimonas, Succinivibrio, Syntrophobacter, Syntrophomonas, Sutterella, Saponavida, Thermobacteroides, Thermosipho, Thermotoga, Tissierella, Wolinella, Zymophilus, Desulfobacter, Desulfobacterium, Desulfobulbus, Desulfococcus, Desulfomicrobium, Desulfomonas, Desulfomonile, Desulfonema, Desulfosarcina, Desulfotomaculum, Desulfovibrio, Desulfurella, Desulfuromonas, Thermodesulfobacterium, Acidaminococcus, Megasphaera, Syntrophococcus, Veillonella, Coprococcus, Peptococcus, Peptostreptococcus, Ruminococcus, Sarcina, Clostridium, Amoebobacter, Chromatium, Lamprobacter, Thiocapsa, Thiocystis, Thiodictyo, Thiopedia, Thiospirillum, Ectothiorhodospira, Rhodobacter, Rhodocyclus, Rhodomicrobium, Rhodopila, Rhodopseudomonas, Rhodospirillum, Erythrobacter, Methanobacterium, Methanobrevibacter, Methanococcu, Methanococcoides, Methanolobus, Methanolacinia, Methanomicrobium, Methanogenium, Methanospirillum, Methanoplanus, Methanothrix, Methanothermus, Methanocorpusculum, Methanoculleus, Methanohalobium, Methanohalophilus, Methanosarcina, Methanosphaera, Eubacterium, Abiotrophia, Atopobium, Gemella, Granulicatella, Finegoldia, Lactobacillus, Actinomyces, Arcanobacterium, Bulleidia, Collinsella, Cryptobacterium, Holdemania, Rothia, Pseudoramibacter, Mogibacterium, Slackia,* and *Eggerthella*.

4. The method of claim 1, wherein the fermentation mixture has a pH in a range of from about 3 to about 6.5.

5. The method of claim 4, further comprising a step of maintaining a substantially constant pH in the fermentation mixture during the fermenting step.

6. The method of claim 4, further comprising a step of monitoring the pH in the fermentation mixture continuously or periodically during the fermenting step.

7. The method of claim 1, wherein the fermentation mixture has a temperature in a range of from about 25° C. to about 40° C. during the fermentation step.

8. The method of claim 1, further comprising a step of adding a nitrogen source to the fermentation mixture.

9. The method of claim 8, wherein the nitrogen source is added to the fermentation mixture in an amount sufficient to provide an amount of nitrogen in the fermentation mixture in a range of from about 0.01 wt. % to about 10 wt. % of the fermentation mixture.

10. The method of claim 1, further comprising a step of adding one or more vitamins to the fermentation mixture, wherein the one or more vitamins are selected from thiamine, cobalamine, riboflavine, niacinamide, pantothenic acid, biotin, ascorbic acid, retinol, procalciol, tocopherol, folic acid and pyridoxamine.

11. The method of claim 1, wherein the fermenting step is a continuous fermentation process.

12. The method of claim 1, wherein the fermentation mixture is agitated during the fermenting step.

13. The method of claim 1, further comprising the steps of monitoring a partial pressure of hydrogen in the headspace of the reactor and adjusting the partial pressure of hydrogen based on the monitored partial pressure of hydrogen in the headspace of the reactor.

14. The method of claim 1, wherein removing hydrogen is carried out using an apparatus selected from a molecular sieve, an adsorbent and a selective membrane.

15. The method of claim 1, further comprising a step of removing carbon dioxide from the gas in the headspace.

16. The method of claim 1, wherein the fermentation mixture has a pH of from about 4 to about 5.5.

17. The method of claim 1, wherein the fermentation mixture has a temperature in a range of from about 29° C. to about 37° C.

18. The method of claim 1, wherein the nitrogen source is added to the fermentation mixture in an amount sufficient to provide an amount of nitrogen in the fermentation mixture in a range of from about 2 wt. % to about 7 wt. %.

19. The method of claim 1, wherein the fermentation mixture has a pH in a range of from about 3 to about 6.5, a temperature in a range of from about 25° C. to about 40° C. and the nitrogen source is added to the fermentation mixture in an amount sufficient to provide an amount of nitrogen in the fermentation mixture in a range of from about 0.1 wt. % to about 10 wt. %.

20. The method of claim 1, wherein the fermentation mixture has a pH of from about 4 to about 5.5, a temperature in a range of from about 29° C. to about 37° C. and the nitrogen source is added to the fermentation mixture in an amount sufficient to provide an amount of nitrogen in the fermentation mixture in a range of from about 2 wt. % to about 7 wt. %.

* * * * *